(12) United States Patent
Curtis

(10) Patent No.: US 7,946,782 B2
(45) Date of Patent: May 24, 2011

(54) DEVICE FOR ANGULARLY COUPLING PROSTHETIC COMPONENTS

(75) Inventor: Michael J. Curtis, Green Bay, WI (US)

(73) Assignee: American Prosthetic Components, Inc., Green Bay, WI (US)

( * ) Notice: Subject to any disclaimer, the term of this patent is extended or adjusted under 35 U.S.C. 154(b) by 1441 days.

(21) Appl. No.: 11/203,512

(22) Filed: Aug. 12, 2005

(65) Prior Publication Data

US 2005/0271462 A1 Dec. 8, 2005

Related U.S. Application Data

(62) Division of application No. 10/626,134, filed on Jul. 25, 2003, now Pat. No. 7,097,666.

(51) Int. Cl.
*A61F 2/64* (2006.01)
(52) U.S. Cl. .............. 403/97; 403/98; 403/113; 623/38; 623/47
(58) Field of Classification Search .............. 623/38, 623/47; 602/27; 403/87, 97, 98, 110, 113
See application file for complete search history.

(56) References Cited

U.S. PATENT DOCUMENTS

| 179,764 | A | | 7/1876 | Briggs et al. | |
|---|---|---|---|---|---|
| 1,030,383 | A | | 6/1912 | Buschman | |
| 3,422,462 | A | * | 1/1969 | Finnieston | 623/38 |
| 3,659,294 | A | | 5/1972 | Glabiszewski | |
| 4,461,045 | A | * | 7/1984 | Shorter et al. | 623/47 |
| 4,568,121 | A | * | 2/1986 | Kashima | 403/82 |
| 5,425,782 | A | * | 6/1995 | Phillips | 623/38 |
| 5,755,812 | A | | 5/1998 | Becker et al. | |
| 5,759,206 | A | * | 6/1998 | Bassett | 623/27 |
| 5,800,564 | A | | 9/1998 | Gelineau | |
| 5,888,232 | A | | 3/1999 | Taylor | |
| 5,888,239 | A | * | 3/1999 | Wellershaus et al. | 623/47 |
| 5,913,901 | A | | 6/1999 | Lacroix | |
| 6,051,026 | A | * | 4/2000 | Biedermann et al. | 623/38 |

FOREIGN PATENT DOCUMENTS

GB 2 298 795 A 9/1996

OTHER PUBLICATIONS

Otto Bock. Three pages from web page www.ottobockus.com/products/op_adapters.asp, as viewed on Oct. 22, 2003. Specifically models 4r56=1 and 4r56. Three pages.
English translation of FR 2 708 848 A1.

* cited by examiner

*Primary Examiner* — Michael P Ferguson
(74) *Attorney, Agent, or Firm* — Brennen Law Office, LLC

(57) ABSTRACT

An angularly adjustable coupler is provided having first and second ends that are in an angularly adjustable mating engagement. The first end has a longitudinal axis and a base with an optionally concave and serrated surface, and can comprise a collared clamp for connecting to a pylon. The second end has a longitudinal axis and a base with an optionally convex and serrated surface, and can comprise a receiver for connecting to a pyramidal adapter. The concave portion of the first end and the convex portion of the second end are complementary to each other. A connector is provided to connect the first and second ends in a selected angular alignment about a fixed axis of rotation. The range of angular alignment of the first and second components spans approximately 50 degrees about the fixed axis of rotation.

3 Claims, 6 Drawing Sheets

BACKGROUND MATERIAL

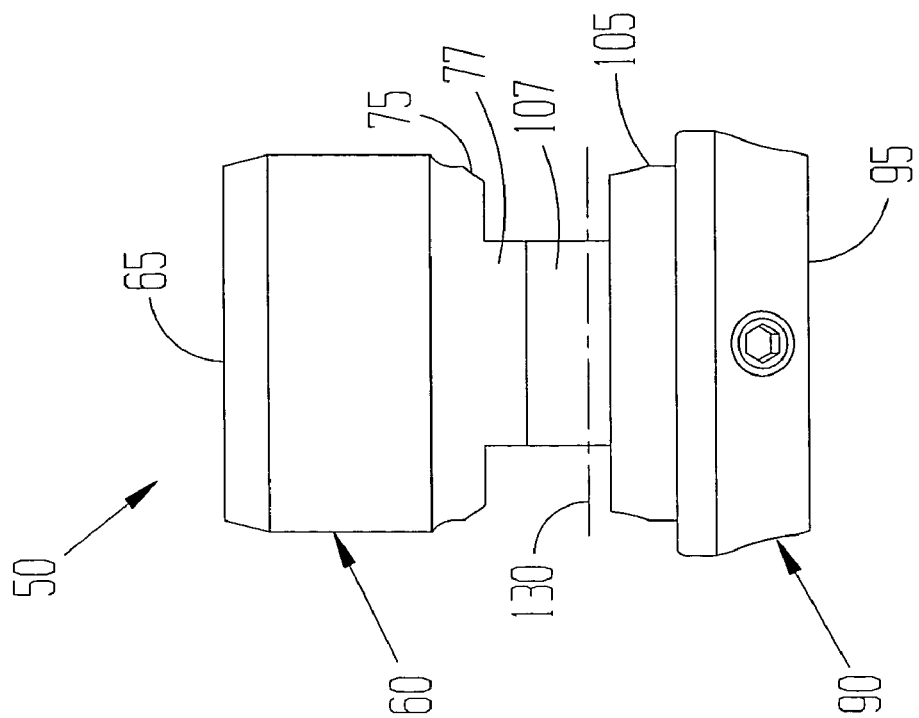
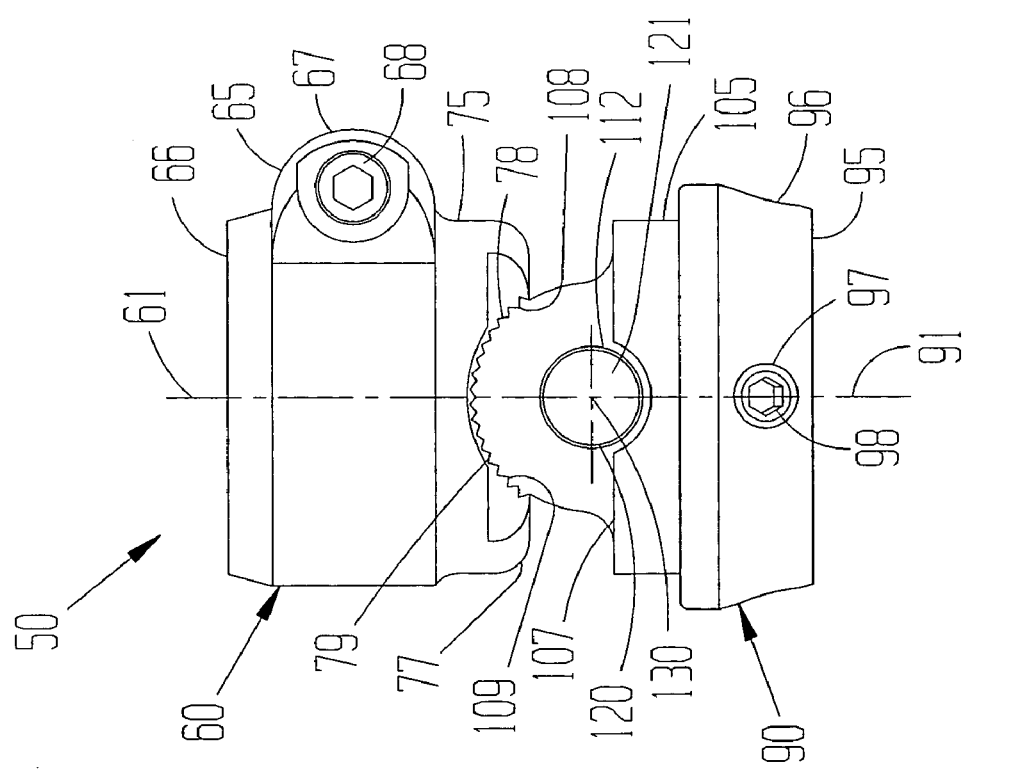

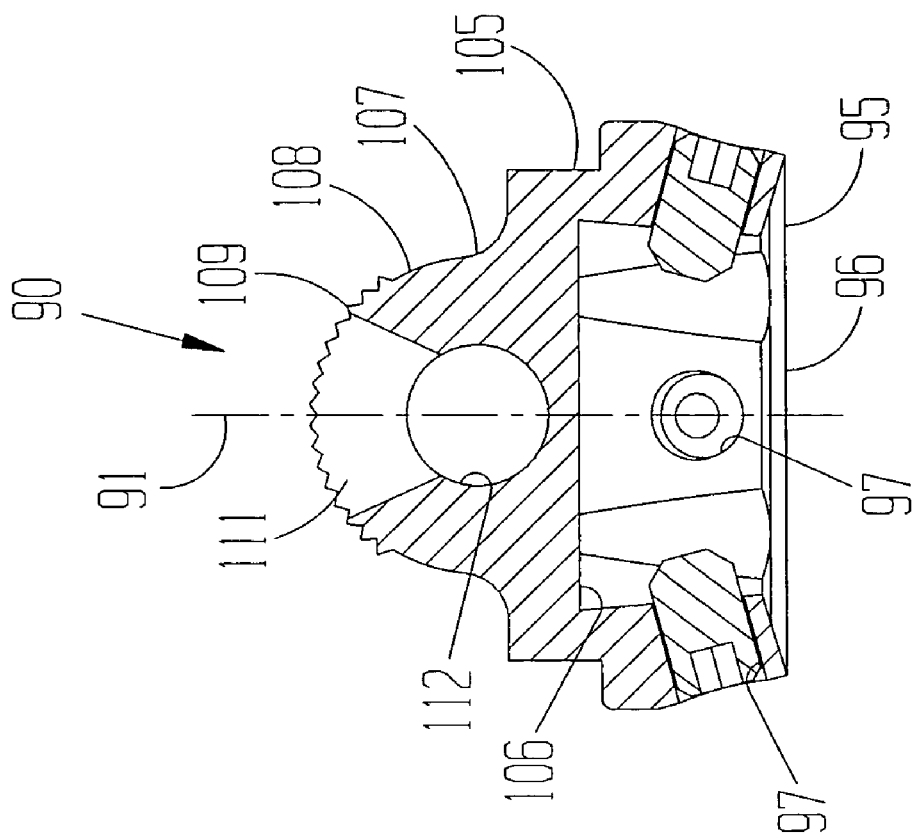
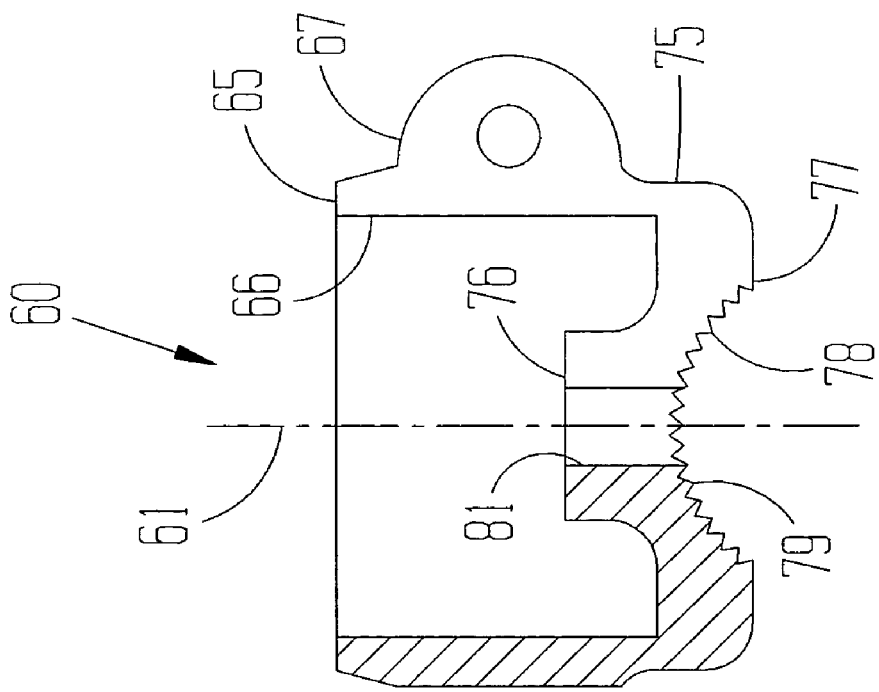

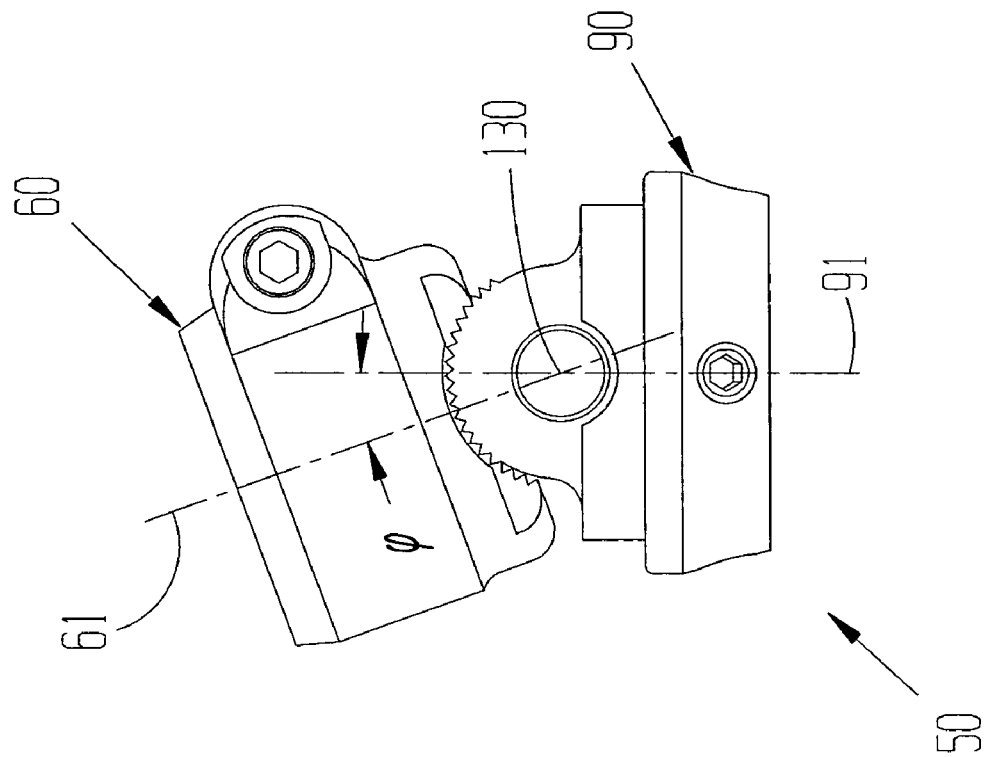
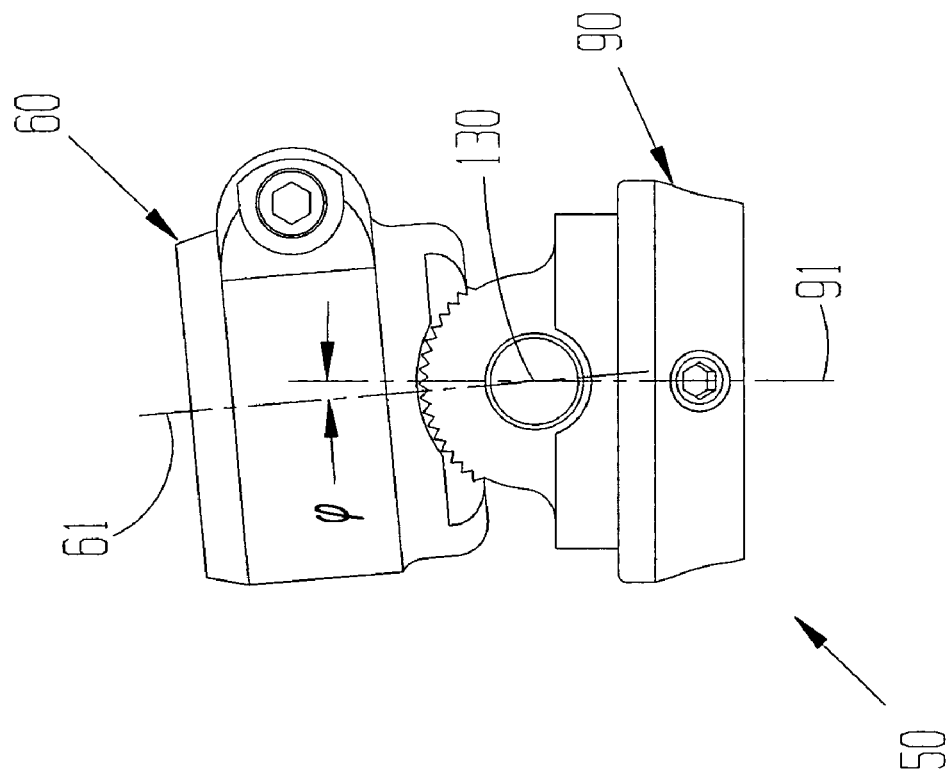

DEVICE FOR ANGULARLY COUPLING PROSTHETIC COMPONENTS

This application is a divisional application of U.S. patent application having Ser. No. 10/626,134 filed Jul. 25, 2003 now U.S. Pat. No. 7,097,666, the contents of which are hereby incorporated herein by reference.

BACKGROUND OF THE INVENTION

1. Field of the Invention

The present invention relates to a device used to couple prosthetic components, and more particularly to adjustably couple prosthetic components in a selected angular relationship.

2. Description of the Related Art

Sometimes, due to accidents, health problems, birth defects, etc., people 5 need to have a limb 6 amputated. The amputated limb 6 terminates in a stump 7. In general, a socket 10 can be formed for a particular stump 7. Those sockets 10 are well known in the art, and each socket 10 has a central axis 11.

Fortunately for people requiring a prosthetic limb, much advancement has been made in the field of prosthetic limbs. Patients now have many choices, including endoskeletal and exoskeletal prosthetic limbs. The present invention relates to endoskeletal prosthetic limbs. That is, limbs comprised of structural components and an optional aesthetic outer shell.

Many prosthetic components are available for use in endoskeletal prosthetic limbs. One of the most common types of prosthetic components is a pylon, which can comprise an aluminum or titanium alloy tube of predetermined length. A clamp can be used to connect to a pylon. Some connectors have two opposed clamps for coupling two pylons. These types of connectors are effective at coupling pylons in a fixed manner. For example, some connectors of this type couple two pylons in a linear manner, where the two pylons are parallel to each other. Other connectors of this type are angled. For example, Otto Bock manufactures a part, having part number 4R56, that provides a fixed and angled connector for two pylons. There is no internal adjustability provided by these types of connectors. Hence, these connectors are incapable of making angular adjustments between two prosthetic components being coupled without additional components.

Another type of existing prosthetic component is a pyramidal adapter, which is adapted to be received within a receiver that has four screws that clamp onto the sides of the pyramid. Using a pyramidal adapter in combination with a receiver is useful in making angular adjustments in both the lateral-medial directions, 15 and 16 respectively, and anterior-posterior directions, 17 and 18 respectively. Yet, the combination of the pyramidal adapter and receiver is only useful for making angular adjustments within a limited range. This limitation is demonstrated in FIG. 1, where the socket 10 has an end 12 that is not perpendicular to the socket central axis 11. Thus, a three prong adapter 20 that is connected to the end 12 of the socket has a central axis 21 that is not parallel with the socket central axis 11. Rather, the three prong adapter central axis 21 is offset from the socket central axis 11 by an angle α. Angle α can have both a lateral-medial component and an anterior-posterior component. Further, the angle α is greater than the angular adjustability possible by using a pyramidal adapter 30 and receiver 45 combination, which is shown as angle β. It is demonstrated that because angle α is greater that the maximum angular adjustability between the pyramidal adapter 30 and fixed receiver 45, angle β, the pylon longitudinal axis 46 is not parallel to the socket central axis 11. This may seriously interfere with a person's ability to walk. Thus, existing pyramidal adapters 30 and receiver 45 combinations may fail to meet the needs of some people.

This type of pyramidal adapter and receiver combination is further illustrated in U.S. Pat. No. 3,659,294. This patent shows an adjustable link for a prosthetic limb. Two parts are shown. One part has a frustopyramidal male end. The second part is a female socket. The socket connects to the frustopyramidal male end in an angular configuration. The link shown in this patent may work well for its intended purpose. However, as discussed above, there is a limit to the adjustability of the link, which can be smaller than necessary depending on a particular patient's needs. Also, the device shown in this patent has no preset adjustments. Further, the device shown in this patent is not adjustable about a fixed axis of rotation.

U.S. Pat. No. 5,888,232 to Taylor discloses an adjusting connector having a pylon or an adapter with a convexly hemispherical protruding portion. A female contact surface with a concavely hemispherical seat is necessary for use with the convexly hemispherical protruding portion of the adapter and pylon. These components are not interchangeable with existing prosthetic components. Further, these components do not rotate about a fixed axis of rotation.

Thus, there exists a need for an angularly variable coupler that solves these and other problems.

SUMMARY OF THE INVENTION

The present invention relates to an angularly adjustable coupler for use with existing prosthetic components, and more particularly to an angularly adjustable coupler having a first end adapted to connect to a first prosthetic component and a second end adapted to connect to a second prosthetic component. The first end and second end are in an angularly adjustable mating engagement.

The first end has a longitudinal axis and has a prosthetic connector, such as a collared clamp, for connecting to a first prosthetic component, such as a pylon. The first end also has a base with a surface that is preferably concave and serrated.

The second end has a longitudinal axis and has a prosthetic connector, such as a receiver, for connecting to a second prosthetic component, such as a pyramidal adapter. The second end also has a base with a surface that is preferably convex and serrated.

The concave portion of the first end and the convex portion of the second end are complementary to each other. A connector is provided to connect the first end to the second end. The connector can be comprised of a pin that extends through a hole in the base of the second end, and a fastener extending through the first end base, partly through the second end base and into the pin, to hold the concave portion of the first end against the convex portion of the second end in a selected angular alignment. That is, the first end longitudinal axis is in an adjustably selected angular alignment with the second end longitudinal axis about the fixed axis of rotation. The range of angular alignment of the first end with respect to the second end about a fixed axis of rotation is approximately 50 degrees.

The present invention is interchangeably usable with existing prosthetic components. Therefore, the prosthesis professional is not limited to using specialty components in order to obtain the benefits of the present invention.

The present invention has a larger range of angular adjustability than an existing pyramidal adapter and receiver combination about a given axis of rotation. This allows the present invention to be used in situations where the maximum angular adjustability range provided by a pyramidal adapter and receiver combination is insufficient.

In accordance with another aspect of the present invention, the coupler is internally adjustable about a fixed axis or rotation. In one embodiment of the present invention, the coupler can be incrementally adjusted about the fixed axis of rotation, yet rigid when the connector is tightened. In that embodiment of the present invention, each successive serration is offset approximately 2.5 degrees.

Other advantages, benefits, and features of the present invention will become apparent to those skilled in the art upon reading the detailed description of the invention and studying the drawings.

BRIEF DESCRIPTION OF THE DRAWINGS

FIG. 2 is a first side view of the present invention.

FIG. 3 is a second side view of the present invention.

FIG. 5 is a cross-sectional view of the first end of the present invention taken along line 5-5 in FIG. 4.

FIG. 6 is a cross-sectional view of the second end of the present invention taken along line 6-6 in FIG. 4.

FIG. 7 is similar to FIG. 2, but shows the first end in a first selected angular alignment relative to the second end.

FIG. 8 is similar to FIG. 2, but shows the first end in a second selected angular alignment relative to the second end.

DETAILED DESCRIPTION OF THE PREFERRED EMBODIMENTS

Figure 1:
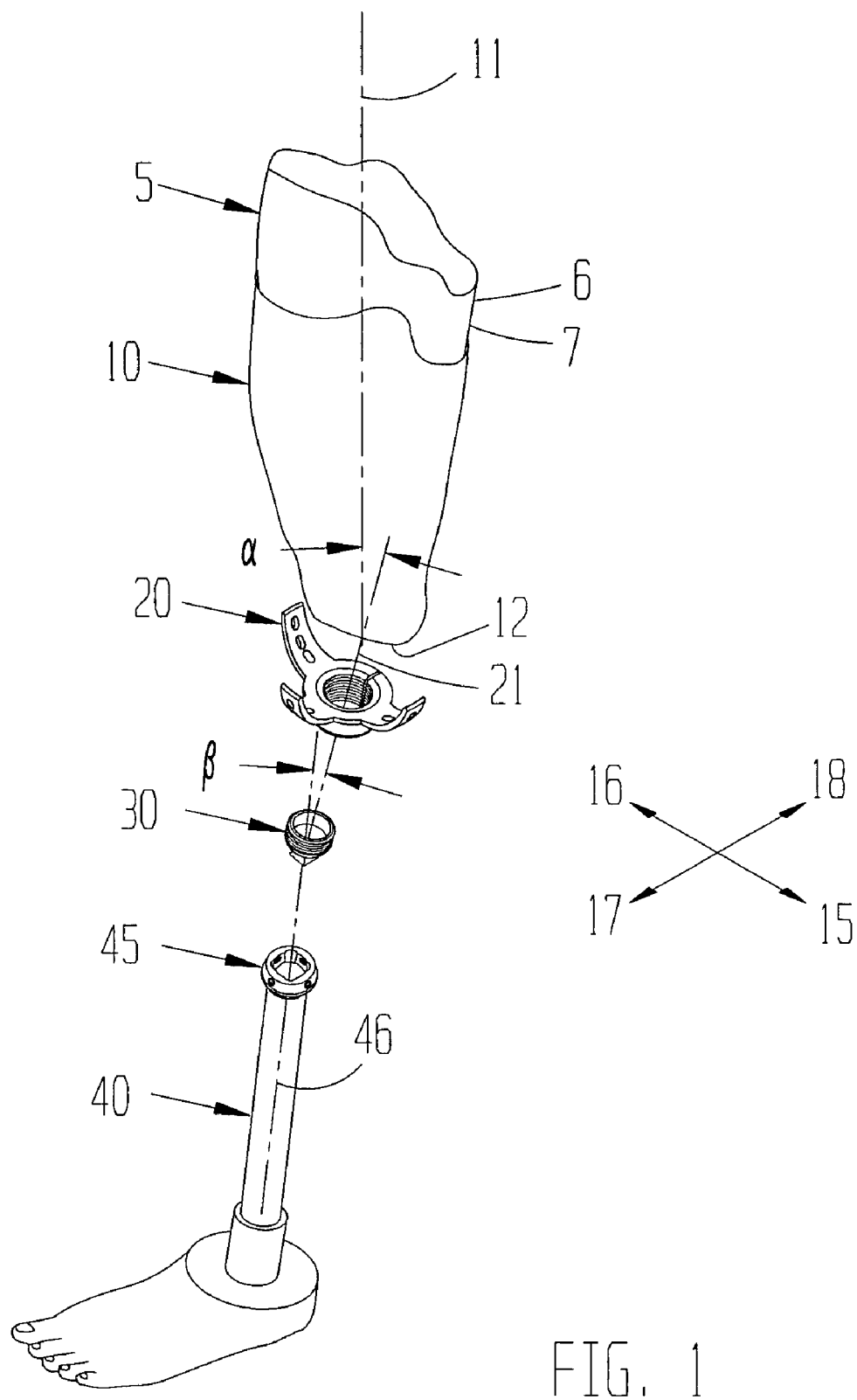
FIG. 1 is a perspective view of background material showing the longitudinal axis of a pylon being angularly offset from the central axis of a socket.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

The present invention relates to and comprises an angled coupler 50. The angled coupler is preferably made of titanium alloy. However, other strong, yet light weight, materials can be used without departing from the broad aspects of the present invention. The angled coupler 50 is preferably made in a computer numerical control (CNC) machining process.

Turning now to FIGS. 2 and 3, it is shown that the present invention has a first end 60. The first end 60 has a first end longitudinal axis 61. The first end 60 also has a connector 65. One preferred connector 65 is a clamped collar, having a collar 66 and a clamp 67. A bolt 68 is provided for inserting into the clamp 67. Turning the bolt 68 into the clamp 67 causes the perimeter of the collar 66 to shrink, and thereby tightens the collar 66 around any item inserted into the first end 60. Other connectors can be used without departing from the broad aspects of the present invention.

The first end 60 of the angled coupler 50 also comprises a base 75. The base 75 has an interior surface 76 and an exterior surface 77, as shown in FIG. 5. The interior surface 76 is accessible through the connector 65. The exterior surface 77 preferably has a concave portion 78. The concave portion 78 has serrations 79 in the preferred embodiment. Alternatively, the concave portion could be smooth (not shown) without departing from the broad aspects of the present invention. A screw hole 81 is through the first end 60 in a direction generally parallel with the longitudinal axis 61. The screw hole 81 is centrally located through the first end 60.

Turning again to FIGS. 2 and 3, it is shown that the angled coupler 50 has a second end 90. The second end 90 has a longitudinal axis 91. The second end 90 also has a connector 95. One preferred connector 95 is an adjustable clamp, comprising a receiver 96 having four holes 97 therethrough. Screws 98 are provided for threadably turning into the holes 97 and into the receiver 96. The second end 90 can have a different type of connector without departing from the broad aspects of the present invention.

The second end 90 of the angled coupler 50 also comprises a base 105. The base has an interior surface 106 and an exterior surface 107, as shown in FIG. 6. The interior surface 106 is accessible through the connector 95. The exterior surface 107 has a convex portion 108. The convex portion 108 has serrations 109 in the preferred embodiment. Alternatively, the convex portion could be smooth (not shown) without departing from the broad aspects of the present invention. A slot 111 is through the second end 90. The slot 111 generally lies in a plane parallel to the longitudinal axis 91 of the second end 90. A pin hole 112 is also through the base 105. Pin hole 112 is generally perpendicular to the longitudinal axis 91 of the second end 90, and also perpendicular to the plane containing slot 111.

Figure 4:
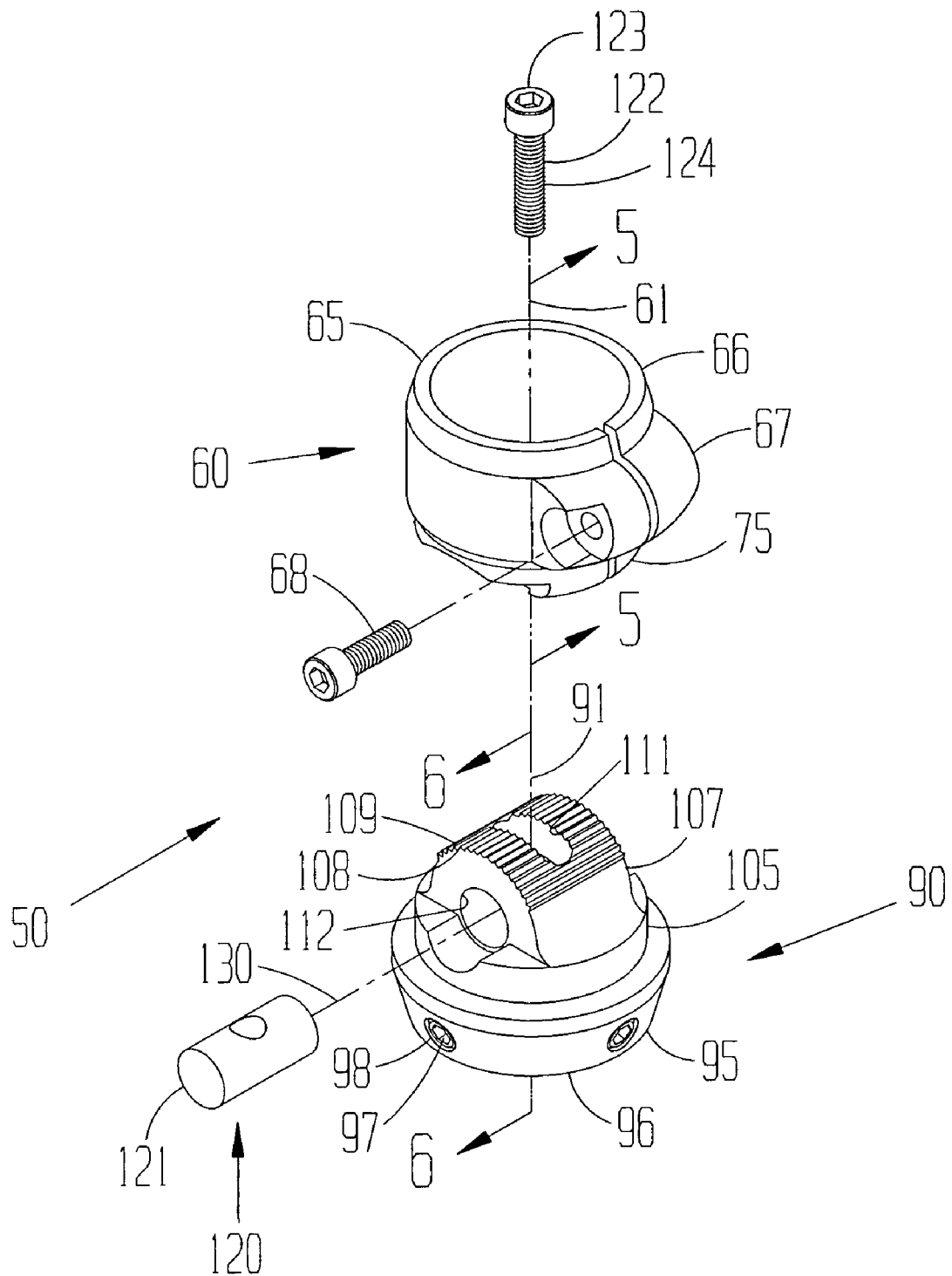
FIG. 4 is an exploded perspective view of the present invention.

Turning now to FIG. 4, a connector 120 is provided. The connector 120 preferably comprises a rotatable pin 121 and a fastener 122. The pin 121 has a longitudinal axis and a side. A hole is in the side in a direction generally perpendicular to the pin longitudinal axis. The hole in the pin 121 is preferably threaded. Two preferred fasteners 122 are screws and bolts, having a head 123 and a shaft 124. The shaft 124 is threaded to threadably turn into the hole in the pin 121. Other types of fasteners may be used without departing from the broad aspects of the present invention.

The first end 60 and second end 90 are adapted to be connected to each other. In a preferred embodiment, the concave portion 78 of the first end 60 mates with the convex portion 108 of the second end 90. Because of this mating engagement, the first end 60 can be connected to the second end 90 in a selected angular alignment about a fixed axis of rotation 130. The connector 120 connects the first and second ends 60 and 90. This is accomplished by inserting the rotatable pin 121 into the pin hole 112 through the second end 60 of the angular coupler 50. The pin 121 is slightly smaller in diameter than the pin hole 112, such that the pin 121 can rotate freely within the pin hole 112. The fastener 122 is inserted through the screw hole 81 through the first end 60 and through the slot 111 through the second end 90. The fastener 122 is threaded into the rotatable pin 121 to securely hold the first end 60 in mating engagement with the second end 90. The head 123 of the fastener 122 abuts the interior surface 76 of the first end 60.

As best shown in FIGS. 7 and 8, connector 120 can hold the first end 60 in a selected angular alignment to angle φ with respect to the second end 90 about a fixed axis of rotation 130. In the preferred embodiment, the pin 121, which is freely rotatable within the pin hole 112, is the fixed axis of rotation 130 about which the first end 60 can be rotated relative to the second end 90. In this regard, the first end longitudinal axis 61 can be selectively angularly aligned with the second end longitudinal axis 91. In the preferred embodiment, the range of selectable angular alignment about the fixed axis of rotation 130 is approximately 50 degrees. Serrations 79 and 109 are provided for incrementally adjusting the angular alignment of the first and second ends 60 and 90. Preferably, each successive serration 79 and 109 provides for an incremental adjustment of approximately 2.5 degrees.

To adjust the angular alignment of the first end 60 with respect to the second end 90, the user first loosens the fastener 122 from the pin 121. The first end is the rotated relative to the second end about the fixed axis of rotation 130 until the desired angular alignment is achieved. Then, the fastener 122 is tightened to the pin 121 to rigidly hold the first end 60 in the desired angular alignment with respect to the second end 90, wherein the first end longitudinal axis 61 is offset from the second end longitudinal axis 91 by angle φ.

Figure 9:
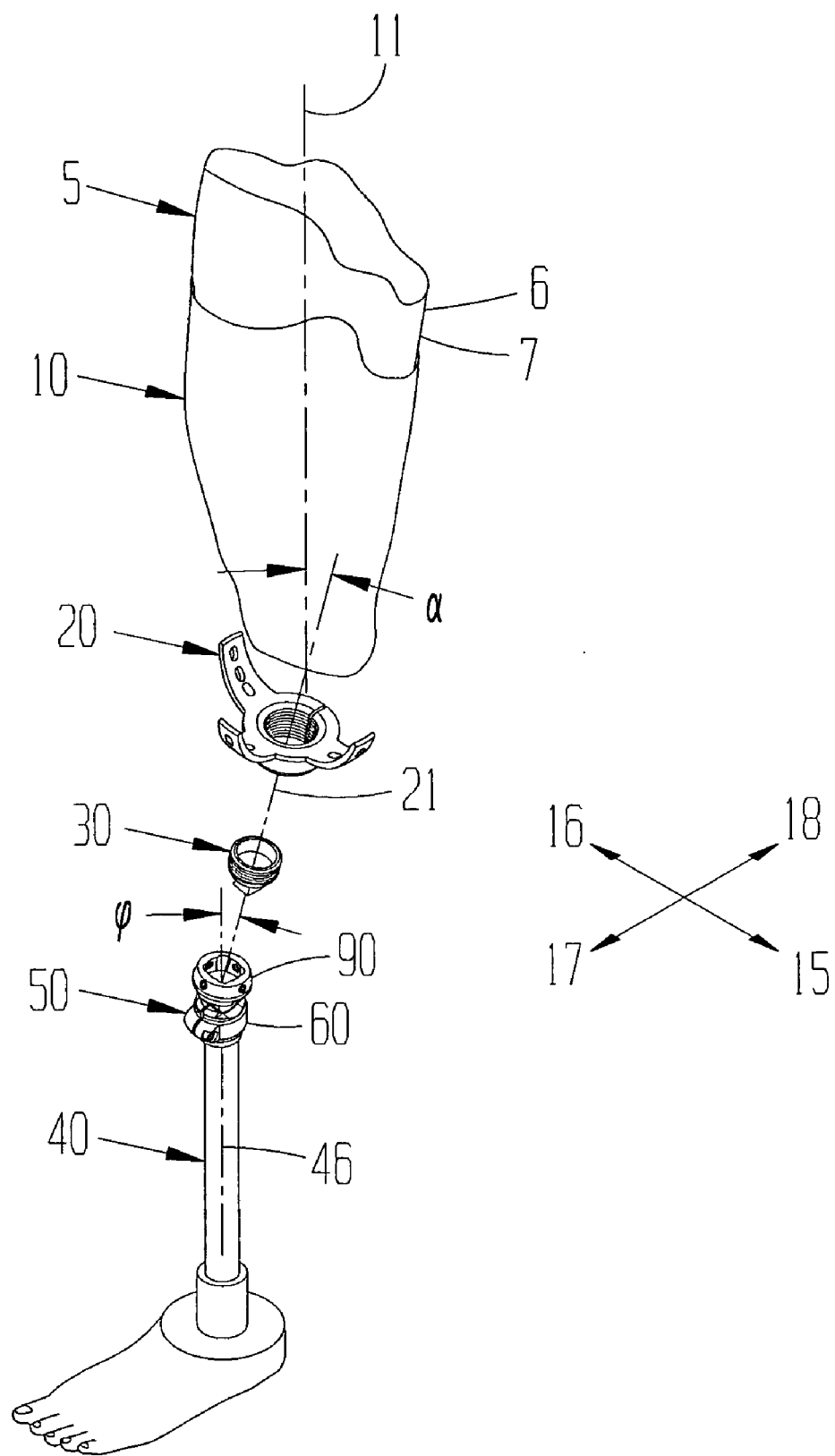
FIG. 9 is an exploded view of the present invention showing a typical set up comprising the present invention and other prosthetic components.

One advantage of the present invention can be seen upon comparison of FIGS. 1 and 9. In FIG. 1, a three prong adapter 20 is aligned to be connected to a socket 10. Because of the particular geometry of the socket 10, and in particular the end 12 of the socket, the central axis 21 of the three prong adapter 20 is angularly offset from the socket central axis 11 by an angle α. The pyramidal adapter 30 is connectable to the three prong adapter 20 in parallel alignment. The pyramidal adapter 30 is angularly connectable to the fixed receiver 45 of a pylon 40. The maximum angular offset between the pylon 40 and pyramidal adapter 30 is angle β. As shown, angle α is greater than angle β. Thus, it is impossible to align the pylon longitudinal axis 46 parallel with the socket central axis 11.

Turning now to FIG. 9, it is shown that the three prong adapter 20 is angularly offset from the socket 10, such that the three prong adapter central axis 21 is offset from the socket central axis by angle α. The angled coupler 50 of the present invention is adjustable to an angle φ, which is approximately equal to angle α. In this regard, the angled coupler 50 can be used to align the pylon longitudinal axis 46 parallel to the socket central axis 11, thereby fostering the person's ability to walk.

Looking more closely at FIG. 9, it is shown that the three prong adapter 20 is attached to the socket 10 in a conventional manner. Depending on the particular socket 10, the socket central axis 11 and the three prong adapter central axis 21 are offset by an angle α, which lies in a plane defined by the socket central axis 11 and the three prong adapter central axis 21. A pyramidal adapter 30 is then rotatably connected to the three prong adapter 20. Because of this rotatable connection between the pyramidal adapter 30 and three prong adapter 20, the pyramid of the pyramidal adapter 20 can be located in any desired rotational orientation with respect to the three prong central axis 21. The pyramid has four edges, which preferably generally form a square. In the preferred rotational orientation of the pyramid, two of the edges generally lie parallel to the plane defined by the socked central axis 11 and the three prong adapter central axis 21 and two of the edges generally lie perpendicular to said plane.

Then, the second end 90 of the angled coupler 50 is connected to the pyramidal adapter 30. Due to the rotatable orientation of the pyramidal adapter, the rotatable pin 121 is generally perpendicular to the plane defined by the socket central axis 11 and the three prong adapter central axis 21. Hence, the angled coupler has a fixed axis of rotation 130 that is generally perpendicular to the plane defined by the socked central axis 11 and the three prong adapter central axis 21, such that the first end 60 can rotate relative to the second end 90 in said plane to a selected angle φ, which is equal to angle α. Therefore, a pylon 40 connected to the first end 60 of the angled coupler 50 will have a longitudinal axis 46 that is generally parallel to, albeit slightly offset from, the socket central axis 11.

It is noted that the angled coupler 50 can be adapted for use with different prosthetic components without departing from the broad aspects of the present invention. For example, a four prong adapter (not shown) could be used in place of the three prong adapter 20. Further, a pyramidal adapter could be integral (not shown) with a three prong adapter rather than being a separate component.

The serrations 79 and 109 provide added structural rigidity to a prosthetic limb constructed with the present invention. However, sometimes, it is desirable to have greater angular flexibility. This can be accomplished in at least two ways. First, the angled coupler 50 could have a first end with a smooth concave surface (not shown) and the second end with a smooth convex surface (not shown). In this regard, the first and second ends could be adjusted to an infinite number of positions about the fixed axis of rotation 130. Second, where a pyramidal adapter 30 is used, the angled coupler 50 can provide the majority of the angular adjustment and the pyramidal adapter 30 can be used to make minor adjustments. In this regard, the pyramidal adapter can be useful for making fine tune adjustments.

Thus it is apparent that there has been provided, in accordance with the invention, a device for angularly coupling prosthetic components that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. An angled coupler comprising:
A. a fastener having a head and a shaft;
B. a first end having:
  i. a first end longitudinal axis;
  ii. a collar with a clamp for receiving and securing an upper prosthetic component to said first end; and
  iii. a first end base connected to said collar, said first end base having a first end base interior surface and a first end base exterior surface, said first end base exterior surface being concave and having serrations, said first end further having a first end hole through said first end base in a direction generally parallel to said first end longitudinal axis and being open to said first end base interior surface, whereby said collar and said first end base interior surface define a first end interior region wherein said head of said fastener engages said first end base interior surface and is accessible only through said first end interior region, and said shaft passes through said first end hole and said first end base exterior surface;
C. a second end having:
  i. a second end longitudinal axis;
  ii. a second end base with a second end base interior surface and a second base end exterior surface, said second end base exterior surface being convex and having serrations adapted to be matingly connected to said first end base exterior surface;
  iii. a slot extending through said second end base in a plane generally parallel to said second end longitudinal axis and longitudinally extending along said convex second base exterior surface and being open to said second end base interior surface and said second end base exterior surface thereby allowing said shaft of said fastener to pass through said slot;
  iv. a second end hole through said second end base in a direction generally perpendicular to said second end longitudinal axis to create a single pivot axis between said first end and said second end, and v. a receiver having set screws, said receiver connected to said second end base and defining a cavity that opens in a direction opposed to said second end base interior surface, said cavity selectably receiving said set screws for releasably retaining a lower prosthetic component; and D. a pin rotatably received in said second end hole being operable about said single pivot axis and having a pin hole that is generally perpendicular to said single pivot axis, said shaft of wherein said fastener is inserted through said first end hole and said slot and into said pin hole in order to adjustably rotate said pin to move said shaft to a desired longitudinal position within said slot and matingly engage the serrations of said first end base and said second end base to rigidly connect said first end and said second end such that said first end longitudinal axis is in a selected angular alignment with respect to said second end longitudinal axis and said first end is angularly adjustable with respect to said second end about said single pivot axis.

2. The angled coupler of claim 1 wherein said slot limits a range of said selected angular alignment about said single pivot axis.

3. The angled coupler of claim 2 wherein said range of said selected angular alignment about said single pivot axis is approximately 50 degrees.

* * * * *